United States Patent [19]

Franken

[11] Patent Number: 4,619,143
[45] Date of Patent: Oct. 28, 1986

[54] APPARATUS AND METHOD FOR THE NON-DESTRUCTIVE INSPECTION OF SOLID BODIES

[75] Inventor: Ferdinand M. J. Franken, GJ Biervliet, Netherlands

[73] Assignee: Dow Chemical (Nederl) B.V., Terneuzen, Netherlands

[21] Appl. No.: 643,915

[22] Filed: Aug. 24, 1984

[51] Int. Cl.$^4$ .............................................. G01N 29/04
[52] U.S. Cl. ........................................ 73/598; 73/602; 73/623; 73/629
[58] Field of Search ................. 73/598, 602, 620, 622, 73/623, 627, 629; 367/49

[56] References Cited

U.S. PATENT DOCUMENTS

| | | | |
|---|---|---|---|
| 3,512,400 | 5/1970 | Lynnworth | 73/598 |
| 4,274,288 | 6/1981 | Tittman | 73/602 |
| 4,412,315 | 10/1983 | Flournay | 73/623 |

*Primary Examiner*—Howard A. Birmiel

[57] ABSTRACT

The non-destructive testing of solid bodies is conducted by generating a transverse, ultrasonic surface wave in the solid body being inspected, said surface waves having sufficient different frequencies such that they travel at different depths through the body being inspected; receiving at least a part of the reflected portion, if any, of the surface waves, the reflected portion consisting of at least two surface waves having sufficiently different frequencies such that these waves travelled at distinctly different depths through the solid body and filtering and measuring or analyzing the reflected portion of the surface waves to determine if a defect or discontinuity exists in the solid body and the depth or severity of the defect or discontinuity. The apparatus for conducting said non-destructive testing comprises a means for generating the ultrasonic surface waves; a means for receiving at least a part of the reflected portion, if any, of the surface waves and a detector means for measuring or analyzing the reflected portion of the surface wave.

11 Claims, 4 Drawing Figures

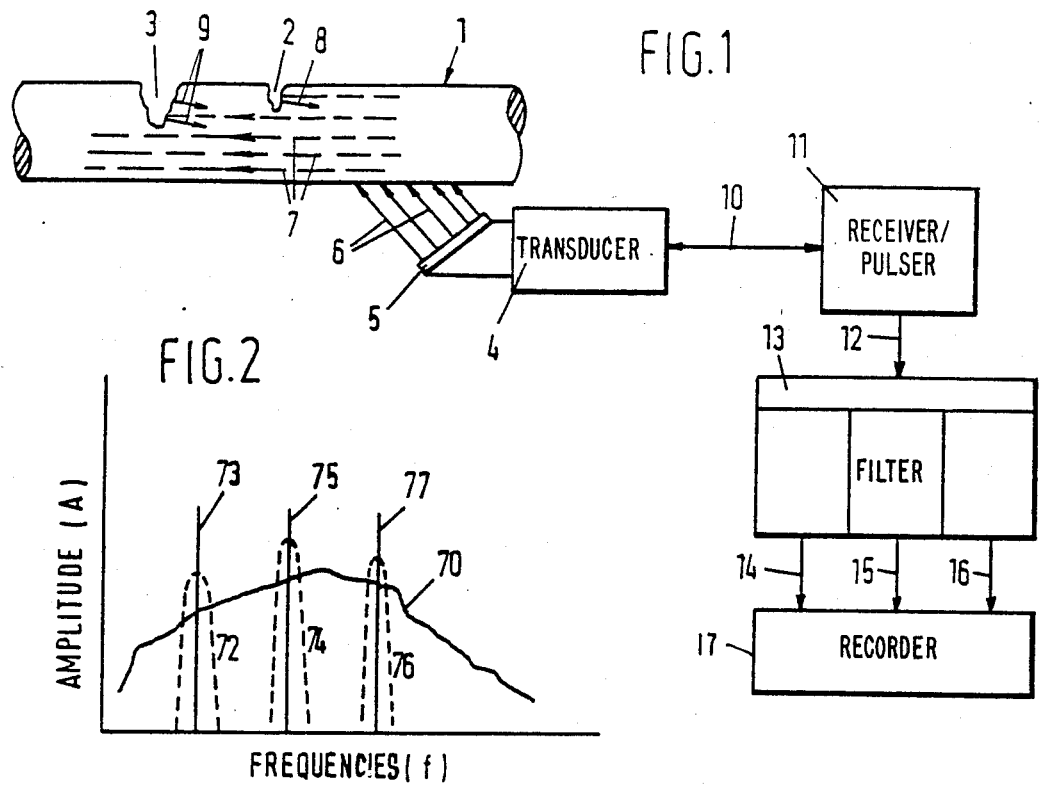
FIG.1
FIG.2
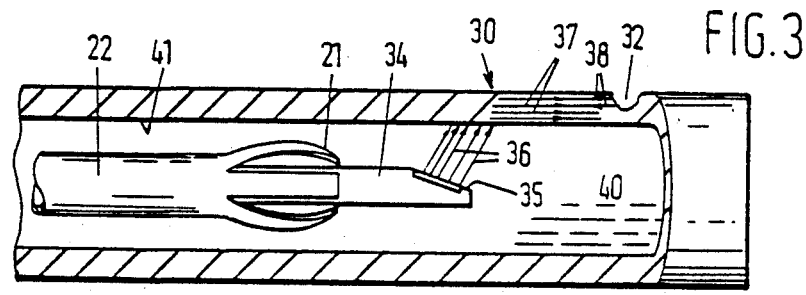
FIG.3
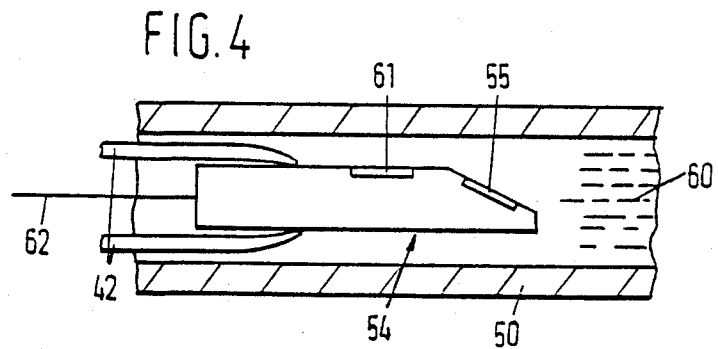
FIG.4

APPARATUS AND METHOD FOR THE NON-DESTRUCTIVE INSPECTION OF SOLID BODIES

The present invention relates to an apparatus and method for the non-destructive inspection of a solid body, and, more particularly, to an apparatus and method which employ ultrasonic waves to inspect a solid body for corrosion or other defects.

It is often desirable to inspect a solid using non-destructive testing techniques in order to predict and prevent the complete failure of the solid during its use. For example, in the operation of a shell and tube or similar type heat exchanger, it is generally desirable to periodically inspect the tube walls for pitting or other defects which are often caused, or at least assisted, by the corrosive liquid(s) flowing through the tube and/or shell portions of the heat exchanger. If not previously detected and repaired, such pitting or other defects often propagate through the entire tube wall, thereby causing the undesirable mixture of the fluids flowing through the tube and shell portions of the heat exchanger.

Heretofore, various methods and apparatus have been proposed to inspect a solid for imperfections. For example, due to the different electrical properties exhibited by a solid material and any imperfection existing therein, electrical means such as eddy current techniques have been employed to detect defects in the surface of the solid. Unfortunately, the described methods are not suitably employed for detecting defects within the interior of the solid or the shell side of the tubes in a shell and tube heat exchanger. Similar disadvantages exist with the photographic techniques such as described in U.S. Pat. No. 4,249,810. In addition, the stray flux techniques which use magnetic field to inspect a solid body can only be employed in detecting defects on the inside of a tubing.

Alternative methods and apparatus for inspecting a solid body employ ultrasonic waves and pulse-echo techniques. For example, in one such method, an ultrasonic wave is transmitted normal, i.e., perpendicular, to the entrance surface of the body being tested and any reflected wave received and measured. Although such techniques can effectively determine the thickness of the solid body being tested, the described techniques cannot detect small defects or corroded portions of the body or distinguish between a defect and other anomalies such as welded joints and irregular surfaces.

Another apparatus for detecting defects, e.g., hairline cracks, at shallow depths in solid bodies such as railways is disclosed in U.S. Pat. No. 3,251,220. Said apparatus comprises a means for generating pulses of ultrasonic waves in the solid and a means for receiving at least some of the reflected portion of the generated waves. Unfortunately, the described apparatus cannot suitably be employed in the inspection of thin walled tubing. Specifically, in the inspection of a thin walled tubing using the described apparatus and method, small defects are only identified with difficulty, and small defects are not readily distinguished from large defects. Moreover, the exact location of the defect in the body being inspected cannot be precisely determined using said apparatus.

In view of deficiencies in the apparatus and methods heretofore employed in inspecting a solid body for defects, it would be highly desirable to provide an apparatus and method capable of detecting and indicating the severity of a defect which exists in a solid body, which method and apparatus can suitably be employed in the inspection of the shell side of a thin wall tubing of a shell and tube heat exchanger.

Accordingly, in one aspect, the present invention is such an apparatus for inspecting a solid. Said apparatus comprises (1) a means for generating transverse surface waves in the solid at sufficiently different frequencies such that the generated surface waves travel at different depths through the solid being inspected and (2) a means capable of receiving at least a part of the reflected portion of surface waves. To determine if any defects exist in the body and the severity thereof, the apparatus includes a detector means capable of measuring or analyzing the reflected portion of the surface waves, said measured portion consisting of the reflected portion, if any, of at least two surface waves having sufficiently different and distinct frequencies such that the reflected portions, if any, of these waves indicate the depth and/or severity of any defect or discontinuity in the solid body.

In another aspect, the present invention is a method for inspecting a solid. The method comprises the steps of (1) generating transverse surface waves in the material to be inspected, said surface waves having sufficiently different frequencies such that they travel at different depths through the material being inspected; (2) receiving at least a part of the reflected portion, if any, of surface waves, the reflected portion consisting of at least two surface waves having sufficiently different frequencies such that these surface waves travelled at distinctly different depths through the solid and (3) filtering and measuring or analyzing the reflected portion of the surface waves to determine if a defect or discontinuity exists in the solid body and the depth or severity of said defect or discontinuity.

The apparatus and method of the present invention are unique in that defects as small as 0.3 mm can be detected in a thin, solid body, e.g., a body having a thickness of up to 5 millimeters (mm), and the severity of said defects measured without having direct physical contact to the surface in which the defect exists. For example, the apparatus and method are particularly suitable for inspecting the outer side of the thin walled tubing such as the shell side of the tubing used in a shell and tube heat exchanger without having physical access thereto. Therefore, tedious and laborious inspection techniques, e.g., visual inspection, are effectively eliminated. Moreover, small or hairline cracks are immediately and accurately detected by the apparatus and method of the present invention.

In a particularly preferred embodiment, the apparatus is a means for inspecting the outer surface of a tubing such as the thin walled tubing of a shell and tube heat exchanger. The apparatus comprises a tranducer means capable of generating, at spaced intervals, pulses of ultrasonic surface waves having different frequencies over essentially the complete circumference of the tubing while continuously travelling through the interior of the tubing being inspected; a detector means, which may or may not be the transducer means, capable of receiving at least a part of the reflected portions of surface waves; and a detector means for measuring the reflected portion, if any, of said waves; the measured portion consisting of at least two surface waves having sufficiently different and distinct frequencies such that the depth and/or severity of any defect or discontinuity in the tubing is determined.

In operation, the transducer means travels through the interior of the tubing while generating pulses of an ultrasonic, surface wave and receiving the reflected portions thereof at conditions such that the location and/or the severity of the defect or discontinuity can be detected. In a preferred embodiment, the transducer means comprises a rotatably mounted crystal and the crystal is continuously rotated as it travels through the interior of the tubing.

Understanding of the invention will be facilitated by referring to the accompanying drawings, in which:

FIG. 1 is a schematic representation, partly in cross-section, of an embodiment of the present invention.

FIG. 2 is a graphical representation of the reflected waves of a highly damped transducer with the filtered portions thereof being indicated.

FIG. 3 is a schematic representation, partly in cross-section, of a preferred embodiment of the present invention useful in inspecting thin walled tubing commonly employed in shell and tube heat exchangers.

FIG. 4 is a schematic representation, partly in cross-section, of an especially preferred apparatus of the present invention particularly useful for inspecting both the inner and outer surfaces of a tubing such as the shell and tube sides of the tubing in a shell and tube heat exchanger.

Referring more particularly to the drawings, FIG. 1, which represents an embodiment of the present invention, depicts a solid or essentially solid body 1 having a defect 2 and a comparatively larger defect 3. A transducer means 4 has a crystal 5 capable of generating logitudinal ultrasonic waves 6 of a plurality of different frequencies. The crystal 5 and solid body 1 are positioned at an angle such that the ultrasonic waves 6 impinging on solid body 1 generate transverse, ultrasonic surface waves, travelling through the solid body 1.

As used herein, the term "surface wave" means a wave which travels parallel to the surface of the body being inspected, i.e., the angle of incidence is such that the wave travels at an essentially constant depth, with respect to the surface of the solid body. To generate surface waves, the angle of incidence of the crystal with respect to the solid body is dependent on the material of construction of the body and the medium through which the waves travel prior to impinging on said body. As an example, when this material is water and the body is constructed of carbon steel, the angle of incidence is 27.5°. In this invention, the different frequencies of the longitudinal, ultrasonic waves generated by crystal 5 are selected such that the generated surface waves 7 travel at different depths through solid body 1. Specifically, the surface waves of higher frequencies travel near the surface of initial wave penetration only whereas the surface waves of lower frequencies penetrate deeper within the solid body and travel up to nearer the surface opposite from initial wave penetration. (For example, a range of frequencies can be selected such that the generated surface waves travel through the entire body being inspected.) Any defect or other discontinuity existing in solid body 1 will reflect at least a portion of the surface waves 7 striking or impinging upon said defect or discontinuity. Transducer means 4 receives, as an echo, at least a portion of these reflected waves. This echo received by the transducer will contain those frequencies of the initially generated surface waves which have been reflected by any defect or other discontinuity in the solid body being inspected.

A measurable signal, e.g., electrical voltage, which corresponds to the frequencies of the waves being received by the transducer means 4 is transmitted to a receiver/pulser means 11 by lead 10. The received signal is transmitted by lead 12 to filter means 13 which is capable of filtering the signal representing the broad bands of reflected waves into separate signals representing the reflected portions of at least two surface waves having sufficiently different frequencies such that the reflected waves correspond to surface waves which travel at distinctly different depths through the solid body 1. In the illustrated embodiment, the filters are selected such that signals representing surface waves of three distinct frequencies are filtered and separated. The separated signals of the distinct, surface waves are fed by means of leads 14, 15 and 16 to recorder or analyzer means 17.

In operation, the receiver/pulser means 11 creates an electrical signal, at specifically spaced intervals, which is fed by means of lead 10 to transducer means 4. The pulse signal causes crystal 5 to produce ultrasonic, longitudinal waves 6 of different frequencies. The transducer means 5 is placed at an angle to the solid body 1 such that the ultrasonic, longitudinal wave 6 impinging on solid body 1 generates only surface waves 7 (i.e., essentially no shear waves are generated). Due to their different frequencies, the generated, surface waves 7 travel at different depths through the solid. Specifically, the penetration depth is inversely proportional to the frequency of the ultrasonic, surface waves; with the waves having the higher frequencies travelling nearer the surface of penetration and the waves having the lower frequencies penetrating deeper within solid body and travelling through the solid body closer to the surface opposite initial wave penetration. As the generated surface waves 7 travel through the solid body 1, a portion of those waves which impinge or strike a defect or other discontinuity in the solid are reflected by said defect or discontinuity. The frequencies of the reflected waves are essentially identical to frequencies of the surface waves being reflected and will therefore indicate the depth and/or severity of the defect or other discontinuity in the solid body. Specifically, a small defect such as the defect 2 in solid body 1 will reflect only those surface waves having a sufficiently low frequency so as to travel near the surface opposite the penetration of the waves in the solid body. Alternatively, a relatively more severe defect such as the defect 3 in the solid body 1 will reflect surface waves having a low frequency as well as surface waves having a comparably higher frequency.

The reflected portion of the surface waves travelling through the body 1 are received by the transducer means 4 and a measurable signal, e.g., electrical voltage, corresponding to the character, e.g., frequency and amplitude, of these reflected waves is transmitted to the receiver/pulser means 11 by means of line 10. From receiver/pulser means 11, the signal is fed by means of line 12 to filter means 13. In filter means 13, the signal corresponding to the broad band of reflected waves is filtered into separate signals corresponding to the reflected portion of at least two waves having sufficiently different frequencies so that they travel at distinctly different depths through the solid body being inspected. Although in the practice of the present invention, it is only necessary to filter the signal representing the broad band of reflected waves into separate signals corresponding to reflected waves of two different frequencies, it is generally advantageous to filter the broad signal into three separate signals corresponding to reflected portions of three waves having separate and different frequencies. Specifically, in the illustrated embodiment, signals corresponding to the reflected portion of (1) a surface wave having a relatively low frequency such that it travels up to and through the solid body near the opposite surface of wave penetration, (2) a surface wave having a comparably high frequency such that it travels nearer the surface of initial penetration and (3) a surface wave having a medium frequency such that it travels essentially through the solid body up to a depth between those of (1) and (2) are filtered and separated from the remainder of the signal corresponding to the broad band of reflected surface waves received by transducer 5. In such manner, the presence and/or absence of a defect at a particular depth in the solid body is indicated.

FIG. 2 is a graphical representation of the amplitude plotted versus frequency of a typical wave generated by the transducer means 4 and the portions of said waves which are to be filtered. Specifically, curve 70 represents the broad band of the initial wave generated by the transducer means 4. The frequencies indicated by lines 73, 75 and 77 are sufficiently different such that the ultrasonic waves having these different frequencies travel at distinctly different depths through the solid body being inspected. The dotted curves 72, 74 and 76 represent the band of frequencies to be filtered. Reflected waves having frequencies within the designated bands will indicate the severity and/or the location of the detected defect. Specifically, if there is no defect or other discontinuity existing in the outer portion of the tube wall, there will be essentially no reflected waves, thereby indicating that there are no defects in the solid body. Alternatively, generated surface waves of low frequencies which are reflected by a small defect will be indicated within the band of frequencies 72 which corresponds to the reflected portions of waves having a lower frequency. Alternatively, defects of relatively greater severity will also reflect waves of relatively higher frequencies which are indicated by the presence of a signal within the band of frequencies 74. A defect of yet greater severity will also reflect waves of even higher frequencies which are indicated by a signal corresponding to the band of frequencies 76. By periodically inspecting the solid, the propagation and/or growth of a shallow defect in the tube can be noted over extended periods of operation.

In a conventional operation of the apparatus depicted in FIG. 1, the entire solid body is inspected in a continuous operation by continuously moving the transducer means 4 over the surface of the solid body 1 while continuously, at spaced intervals, generating pulses of ultrasonic waves and receiving the reflected portions of these generated waves. In this continuous operation, the time interval established for receiving the reflected waves is advantageously gated so as to omit the undesirable portion of the reflected waves.

In a preferred embodiment, the apparatus and method of this invention are employed in the inspection of thin walled tubing such as that found in a shell and tube type heat exchanger. The apparatus and method are particularly useful in inspecting for defects or other discontinuities on the shell side of the tubing. Such preferred embodiment is represented schematically in FIG. 3 which depicts a thin walled tubing 30 having defect 32 therein. A transducer means 34 having crystal 35 is rotatably mounted to a hollow rod or cylinder 22 using clips and/or fingers 21. Leads for connecting the transducer means with the pulser/receiver means (not shown) extend through this hollow cylinder. The transducer means 34 and crystal 35, in combination with said pulser/receiving means, are capable of creating, at spaced intervals, an ultrasonic wave having different frequencies. The frequencies of longitudinal, ultrasonic waves and the position (i.e., angle) of crystal 35 in relation to the tube wall are such that upon the impingement of the longitudinal ultrasonic waves 36 generated by the crystal 35 on the inner surface of tube 30, transverse surface waves 37 are generated at various depths throughout the tube wall. The tube is often and preferably filled with an acoustical conductive liquid 40 such as water to improve the coupling (i.e., transmittance of the waves) between the transducer surface and the inner surface of the tubing.

In operation, the crystal 35 transmits, at spaced intervals, a longitudinal wave 36 of different frequencies to the inner surface 41 of tube or pipe 30. The angle of the crystal 35, in relation to the wall of the tube or pipe 30, is such that this longitudinal wave 36 generates ultrasonic transverse surface waves 37 of different frequencies within the wall of tubing 30. The different frequencies of the surface waves generated by wave 36 are selected such that these generated surface waves travel at different depths through the tube. At least a portion of the surface waves striking or impinging upon defect 32 are reflected thereby. These reflected waves are subsequently received by transducer means 34 which transmits a measurable signal, e.g., an electric voltage, corresponding to the characteristics of the reflected waves to the pulser/receiver means for subsequent filtering into separate signals corresponding to at least two waves of sufficiently different frequencies such that the location and/or severity of a defect in the shell side of the tubing can be detected. Subsequent analysis of the separated signals indicates the presence of a defect, if any, and its severity and/or location.

In the described operation wherein the outer portion of the tubing is inspected for defects, while the transducer means travels through the interior of the tubing, the transducer means is continuously rotated, while generating pulses, at spaced intervals, of ultrasonic waves, and receiving, at spaced intervals, the reflected portions thereof. As previously mentioned, the interval for receiving the reflected signal is preferably gated to eliminate the undesirable portion of the reflected wave. The speed at which the transducer means travels through the tubing, the rotational speed of the transducer and the spaced intervals for the pulse and reception of the ultrasonic waves are interrelated and established such that any defect or discontinuity in the tubing can be detected and its severity and/or position indicated. In general, to accurately locate and determine the severity of any defect or other discontinuity, the ultrasonic, surface waves of at least 5, preferably 10, individual pulses are reflected by the defect or other discontiniuty. The speed of the transducer means through the tubing, the speed of rotation, the spaced interval for pulsing and receiving the ultrasonic waves and the gating of these intervals are set accordingly. These will vary depending on a variety of factors including the liquid acoustical means, if any, employed and the construction of material of the tubing, rotational speeds and pulse/receive cycle times most advantageously employed for tubing of different wall thicknesses and/or interior diameters can be readily determined by those skilled in the art by conventional practice supplemented using simple, experimental techniques.

FIG. 4 depicts an alternative and preferred embodiment of the present invention wherein defects on both the outer and interior surface of the tubing can be detected. In said embodiment, a wave generating means 54 is disposed within a thin walled tubing 50. Wave generating means is rotatably mounted by means of fingers or clips 42 and is connected to pulser/receiving means (not shown) by means of lead 62. Conduit or tubing 50 is filled with water 60 or other acoustical enhancing liquid. Wave generating means 54 comprises (1) a crystal 55 for creating longitudinal, ultrasonic waves which impinge on the interior surface and are transmitted as surface waves at different depths through the walls of conduit 50 and (2) a means 61 for measuring the wall thickness of the tube and/or defects inside of the tube, such as an eddy current generating means or a means for generating ultrasonic waves normal to the tube surface.

Most preferably, the device of the present invention is employed in combination with an eddy current generating means and a means for generating longitudinal waves through the solid body, normal to the surface of the wave penetration. In such manner, the wall thickness and any larger areas of erosion and/or pitting can be determined in addition to inspecting the inner and outer (i.e., shell side) portions of the tube for defects.

In operation, any defects on the outer or shell side of conduit 50 are detected by measuring and analyzing the reflected portion of the ultrasonic waves generated by crystal 55 and traveling as surface waves through tubing 50 by the techniques hereinbefore described. Defects which are located on the inner side of the tubes can be determined by conventional techniques using means 61. Such techniques are well known in the art and reference is made thereto for the purposes of this invention.

With regard to the various components useful in the present invention, the transducer means, including the crystal and pulser/receiver means are suitably components capable of (1) generating longitudinal ultrasonic waves of the desired frequencies at spaced intervals and (2) receiving, at spaced intervals, the reflected portions of said waves. By the term "ultrasonic" it is meant sound vibrations beyond the audible frequency. The term "longitudinal" is used conventionally herein and refers generally to waves in which the particles of the medium through which the wave travels move in the same direction as the wave. The desired frequencies used in the application of the present invention are dependent on the body being tested and the desired depths at which the transverse surface waves generated by the longitudinal waves travel through said body. The term "transverse" is used conventionally herein and refers generally to those waves wherein the particle of the medium moves perpendicular to the direction of wave movement. As an example, in the inspection of a thin walled, carbon steel, tubing having a wall thickness from 2 to 4 mm, transverse ultrasonic waves exhibiting a frequency from 1,000,000 to 4,000,000 cycles/second, which travel forward through the body at a speed of approximately 3300 meters per second are advantageously employed. In general, the frequencies are selected such that surface waves are generated throughout the entire depth of the body being inspected and the severity and/or location being determined by properly selecting the frequencies to be filtered. Inspection of thicker or thinner bodies and/or the inspection at different depths through the body is readily achieved using ultrasonic waves of different frequencies or changing the selected frequencies being filtered.

In general, the pulses of ultrasonic waves from the pulser/receiver unit are in the form of an electrical signal having a predetermined frequency which will generally vary from one million cycles per second up to and exceeding twenty million cycles per second. The output from the pulser/receiver means is coupled with the transducer means by a transmission line such as a flexible coaxial cable. Mercury or other conductive fluid is advantageously employed to make the necessary electrical contact between the transducer means and cable when the transducer means is rotatably mounted such as depicted in the devices illustrated in FIGS. 3 and 4. The transducer preferably comprises a dampened and electronically matched crystal. Although the transducer, including the crystal, can be of any of a variety of different materials, in general, it is an electrical acoustical device such as a piezoelectric crystal, capacitor or laser. Alternatively, a magnetostrictive transducer can be employed. To most effectively concentrate the generated ultrasonic energy as surface waves in the tube or other material being tested, a focused probe is often advantageously employed as the transducer means. The transducer means is also capable of receiving the reflected portions of the generated surface waves and returning the electrical signal generated by these reflected waves to the receiver/pulser means.

Although the transducer and the pulser/receiver means are indicated as two units in the drawings, a single unit comprising the transducer and pulsing receiver means can be employed as a wave generating means. Similarly, a transducer means can be employed exclusively to generate the pulses of ultrasonic waves and a separate transducer means employed to receive the reflected portions of said generated waves. Such modifications and/or variations in the transducer and receiver/pulser means are well known in the art and reference is made thereto for the purposes of this invention.

The filter means is suitably any means capable of filtering and separating the broad signal corresponding to the reflected waves into separate signals corresponding to waves having sufficiently different frequencies or wavelengths such that the waves travel at distinctly different depths through the solid body being inspected. The desired frequencies of the separated waves will vary depending on a variety of factors including the solid body being inspected and its thickness. For example, in the inspection of thin walled tubing as described above, the filter means advantageously filters and separates the signal corresponding to the reflected portions of the generated ultrasonic waves into bands having center frequencies of 1,000,000; 2,000,000 and 3,000,000 cycles per second. In other operations, the desired wavelengths to be filtered and separated are selected accordingly.

The analyzer means is suitably any means capable of receiving and measuring the filtered signals of the ultrasonic waves. Although the response can be indicated visually such as on a CRT or registering the data on a strip chart, a computer is advantageously employed for the analysis. Devices conventionally employed for such purposes are usful in the practice of this invention. Advantageously, the detectors used in the present invention are sensitive to small charges in electrical currents.

What is claimed is:

1. An apparatus for nondestructively inspecting a wave transmitting solid, said apparatus comprising in cooperative combination (a) means for generating transverse surface waves in the solid which have sufficiently different frequencies such that they travel at different depths through the solid; (b) means for receiving at least a part of a reflected portion of the surface waves; and a detector means for measuring the reflected portion of at least two surface waves having sufficiently different frequencies such that the reflected portion of these waves indicate the severity of a wave reflective discontinuity in the solid body, said apparatus characterized by utility for discriminating the location of discontinuities in the solid concealed from the surface adjacent the wave generating means.

2. The apparatus of claim 1 wherein the transverse surface waves are generated by a transducer means capable of generating longitudinal ultrasonic waves of a plurality of different frequencies, said transducer means being positioned such that the longitudinal waves impinging on the surface of the solid generate transverse ultransonic surface waves travelling at different depths through the body.

3. The apparatus of claim 2 wherein the receiving means is capable of generating a measurable signal corresponding to the broad band of reflected waves.

4. The apparatus of claim 3 wherein the detector means comprises a filter means capable of filtering the signal representing the broad band of reflected waves, if any, generated by the receiving means into separate signals representing the reflected portion of at least two sufficiently different frequencies such that the reflected waves correspond to surface waves which travel at distinctly different depths through the solid being inspected.

5. The apparatus of claim 4 wherein the detector means further comprises a computing means for analyzing the separate signals representing the filtered portion of the reflected waves.

6. An apparatus for nondestructively inspecting the outer surface of a wave transmitting tube, the apparatus comprising in cooperative combination (a) means adapted to move through the interior of the tube being inspected while generating pulses of transverse, ultrasonic surface waves having different frequencies which travel at different depths through the tube wall over essentially the complete circumference of the tube; (b) means for receiving at least a part of a reflected portions of the surface waves; and (c) a detector means for measuring the reflected portions of at least two surface waves having sufficiently different and distinct frequencies such that the severity of a wave reflective discontinuity on the outer surface of the tube can be inspected.

7. The apparatus of claim 6 wherein the wave generating means comprises a transducer means.

8. The apparatus of claim 7 wherein the transducer means comprises a rotatably mounted crystal which is capable of being continuously rotated as it travels through the interior of the tube.

9. A method for nondestructively inspecting a wave transmitting solid for discontinuities including those concealed from the surface inspected, the method comprising the steps of (1) generating ultrasonic surface waves in the solid, said surface waves having sufficiently different frequencies such that they travel at different depths through the solid, (2) receiving at least part of a reflected portion of at least two surface waves having sufficiently different frequencies such that these surface waves travelled at distinctly different depths through the solid; and (3) analyzing the reflected portion of the surface waves to detect wave reflective discontinuities in the solid.

10. The method of claim 9 wherein step (3) comprises analyzing the reflected portion of the surface waves to characterize the severity of discontinuities in the solid.

11. The method of claim 9 wherein the solid is a tube and the method is employed to inspect the outer surface of the tube.

* * * * *